United States Patent
Marelli et al.

(10) Patent No.: US 11,229,794 B2
(45) Date of Patent: Jan. 25, 2022

(54) ELECTRICAL INTERCONNECTION SYSTEM BETWEEN AN INTRINSICALLY EXTENSIBLE CONDUCTOR AND A NOT INTRINSICALLY EXTENSIBLE ONE

(71) Applicant: WISE S.R.L., Milan (IT)

(72) Inventors: Mattia Marelli, Milan (IT); Alessandro Antonini, Milan (IT); Cristian Ghisleri, Soncino (IT); Laura Spreafico, Senago (IT); Sandro Ferrari, Bergamo (IT)

(73) Assignee: WISE S.R.L., Milan (IT)

( * ) Notice: Subject to any disclaimer, the term of this patent is extended or adjusted under 35 U.S.C. 154(b) by 342 days.

(21) Appl. No.: 16/303,667

(22) PCT Filed: May 24, 2017

(86) PCT No.: PCT/IB2017/053056
§ 371 (c)(1),
(2) Date: Nov. 21, 2018

(87) PCT Pub. No.: WO2017/203441
PCT Pub. Date: Nov. 30, 2017

(65) Prior Publication Data
US 2020/0316380 A1    Oct. 8, 2020

(30) Foreign Application Priority Data

May 24, 2016 (IT) .................. 102016000053271

(51) Int. Cl.
*A61N 1/36* (2006.01)
*A61N 1/04* (2006.01)
(Continued)

(52) U.S. Cl.
CPC ........ *A61N 1/36125* (2013.01); *A61N 1/048* (2013.01); *A61N 1/0551* (2013.01); *A61N 1/3752* (2013.01)

(58) Field of Classification Search
CPC .. A61N 1/36125; A61N 1/048; A61N 1/0551; A61N 1/3752
See application file for complete search history.

(56) References Cited

U.S. PATENT DOCUMENTS 9,040,839 B2    5/2015 Furuta et al.
2003/0233133 A1* 12/2003 Greenberg ............. H05K 3/361
                                                              607/36

(Continued)

FOREIGN PATENT DOCUMENTS

| EP | 2963675 A1 | 1/2016 |
| FR | 2712133 A1 | 5/1995 |
| JP | 2012033316 A | 2/2012 |

OTHER PUBLICATIONS

International Search Report and Written Opinion for corresponding Application No. PCT/IB2017/053056 (dated Sep. 6, 2017).

(Continued)

*Primary Examiner* — Amanda K Hulbert
(74) *Attorney, Agent, or Firm* — Troutman Pepper Hamilton Sanders LLP (Rochester)

(57) ABSTRACT

A system is described for obtaining the electrical interconnection between an intrinsically extensible conductor (120) and a not intrinsically extensible one (110), or between two intrinsically extensible conductors. The system is particularly applied in the production of devices implantable in the human or animal body, highly conformable and deformable, for neurostimulation and/or neurorecording.

13 Claims, 6 Drawing Sheets

(51) Int. Cl.
*A61N 1/05* (2006.01)
*A61N 1/375* (2006.01)

(56) References Cited

U.S. PATENT DOCUMENTS

| | | | |
|---|---|---|---|
| 2015/0165219 A1* | 6/2015 | Markham | A61B 5/6847 607/116 |
| 2015/0237711 A1* | 8/2015 | Rogers | H01L 21/6835 174/251 |

OTHER PUBLICATIONS

International Preliminary Report on Patentability for corresponding Application No. PCT/IB2017/053056 (dated May 7, 2018).

* cited by examiner

ELECTRICAL INTERCONNECTION SYSTEM BETWEEN AN INTRINSICALLY EXTENSIBLE CONDUCTOR AND A NOT INTRINSICALLY EXTENSIBLE ONE

This application is a national stage application under 35 U.S.C. § 371 of PCT Application No. PCT/IB2017/053056, filed 24 May 2017, which claims priority of Italy Application No. 102016000053271, filed 24 May 2016, which are hereby incorporated by reference in their entirety.

FIELD OF THE INVENTION

The present invention relates to a system for obtaining the electrical interconnection between an intrinsically extensible conductor and a not intrinsically extensible one; in particular, the system of the invention finds application in the manufacture of devices implantable in the human or animal body, highly conformable and deformable, for neurostimulation and/or neurorecording.

PRIOR ART

In many areas of the field there is a need to establish a stable electrical connection between rigid or at most flexible conductors, such as wires or tracks of printed circuit boards, subjected to mechanical strains such as deformation, vibration or compression. These strains generally act in directions transverse to the ideal line formed by the joining of the two conductors. The solutions developed (also object of patents) are focused on methods of reducing or cancelling the forces on the interface of the interconnection between the two conductors, to prevent fractures in the material that forms the conductor.

In recent years, conductors have been studied and are still under development, which as well as being flexible are intrinsically extensible, i.e. able to undergo (reversible) lengthening in the direction of conduction of electricity; while being usable in any situation requiring a conductor, the primary intended application is for the production of electrodes implantable in the human (and animal) body, which requires that said electrodes can follow all the deformations of the part in which they are inserted, including lengthening and returns to the initial length without loss of continuity and of the main electrical characteristics.

A first method proposed to produce conductors with these characteristics consists in preparing metal lines (wires or thin deposits) with undulating pattern within biocompatible elastomeric polymers, making one or more electrical contacts emerge to the surface of the polymer at predeset points depending on the intended application; when the polymer undergoes the lengthening, the wavy shape of the metal line allows the stretching or shortening thereof. Conductors of this type are described for example in U.S. Pat. No. 7,085,605 B2 and U.S. Pat. No. 7,265,298 B2.

A second approach is described in U.S. Pat. No. 9,107,592 B2, and consists in depositing (with known methods) metal tracks on a pre-stretched elastomer; after the deposit, the elastomer is left to return to its size "at rest" and the metal deposit is geometrically rearranged to follow the contraction thereof.

Finally, another alternative approach is described in the international patent application WO 2011/121017 A1 assigned to the present Applicant. According to this method, the conductive line is created by implanting in an elastic polymer nanometric size aggregates of metals (for example, titanium); the examples provided in the application show that although the deposit consists of discrete particles, electrical continuity is ensured, as well as its retention even after tens of thousands of cycles of lengthening/shortening of the conductor.

Conductors of this type, which can be stretched along the main direction of electrical conduction, are referred to in the present text and in the claims as "intrinsically extensible", or even simply extensible.

The problems of creating contact points between different conductors, mentioned above, are much more complex when one of the two conductors is intrinsically extensible; similar problems are encountered if the two conductors are both of the intrinsically extensible type, but have a large difference in the modulus of elasticity.

The solutions traditionally adopted for connecting rigid or at most flexible conductors are not suitable for these cases where, in addition to the deformations mentioned above, in the contact area there are also longitudinal deformations due to forces acting in opposite directions along the ideal line formed by the joining of the two conductors.

In fact, the interconnection between a soft and extensible conductive structure and a non-extensible one (such as a metal wire), connected to each other and subjected to strains and deformations, is very critical because stresses accumulate mostly at this point, giving rise to mechanical failures and consequent power disruptions.

The problem is further complicated by the fact that, with a view to the biomedical application, and particularly for implants in the human body, the electrical interconnection must be integrated into the smallest possible space and possibly even allow the interconnection of many contacts in parallel.

A possible solution (as described in Bossuyt F. et al, "*Stretchable Electronics Technology for Large Area Applications: Fabrication and Mechanical Characterization*", IEEE Transactions on Components, Packaging and Manufacturing Technology 3, no. 2 (February 2013): 229-35. doi:10.1109/TCPMT.2012.2185792) is to integrate a rigid structure ("armour") in the interconnection region of the extensible part, so as to prevent mechanical stress to act on this area; the armour may for example be a non-extensible sheet integrated into the extensible substrate in the interconnection area or similar measures. This approach is however simply a way to bring the problem to the interconnection between two rigid parts and, requiring the integration of an additional part (armour) into the device, it is not suitable to at the same time solve the problem of reducing the size of the interconnection; for this reason, the use of an armour is not optimal for manufacturing a medical device where miniaturization is a prerequisite.

Patent application US 2003/0233133 A1 describes a system for the electrical interconnection between an integrated circuit and conductive track on a flexible substrate; the system described in this document constitutes an improvement over previous systems, but does not allow the electrical connection with conductive tracks deposited on extensible substrates, as is necessary for the connection of implantable devices in the human or animal body in order to follow the movements thereof.

SUMMARY OF THE INVENTION

The object of the present invention is to provide a system for the creation of a stable electrical contact between an elastic and extensible conductor and a non-extensible one, or between two extensible conductors having different elastic modulus, adapted to relieve stress in the interconnection region between the two conductors without using additional rigid armours.

This object is achieved with a system comprising:

an interconnection board consisting of a non-extensible planar substrate (flexible or rigid), on one functionalized face of which is present at least one conductive track, each in electrical contact, at one end thereof, with at least one conductor external to the system which may be rigid, elastic or in its turn extensible;

an elastic and extensible substrate on a functionalized face of which is present at least one extensible conductive structure;

at least one deposit of an adhesive and electrically insulating material, interposed between the interconnection board and elastic and extensible substrate, which adheres to said functionalized faces at least in part of the zones of said faces free from said at least one conductive track and said at least one extensible conductive structure, establishing the adhesion between said board and substrate while allowing the relative motion thereof and ensuring the contact between said at least one conductive track and said at least one extensible conductive structure, optionally through at least one deposit of an adhesive, elastic and electrically conductive material.

DETAILED DESCRIPTION OF THE INVENTION

Figure 1A:
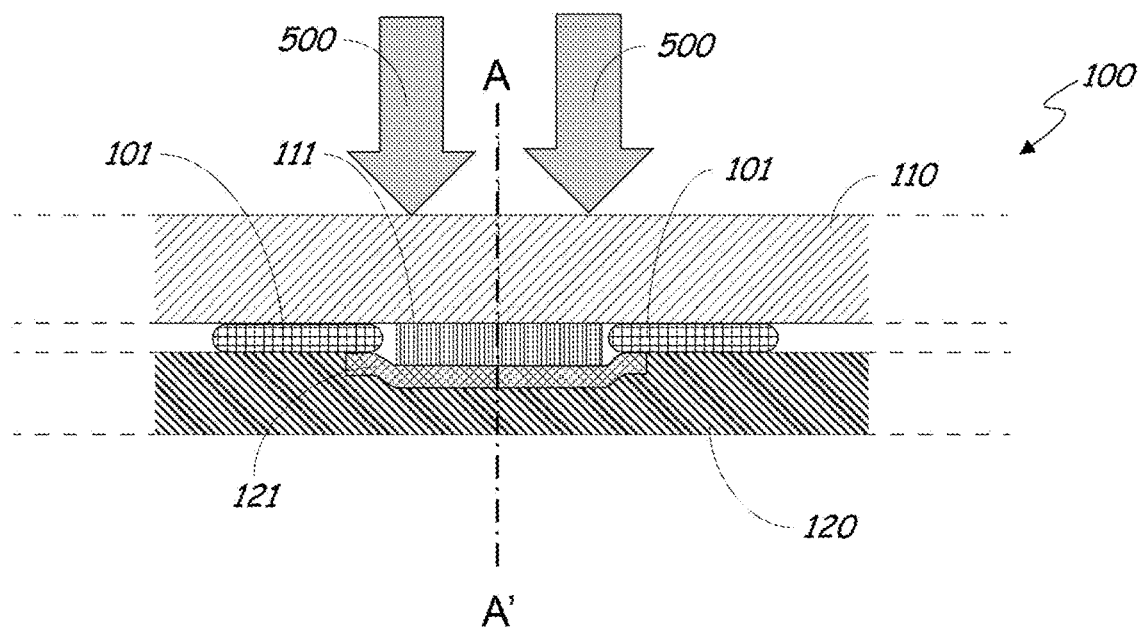
FIGS. 1A, 1A' and 1B show sectional views of a system according to a first embodiment of the invention.
Figure 1A:
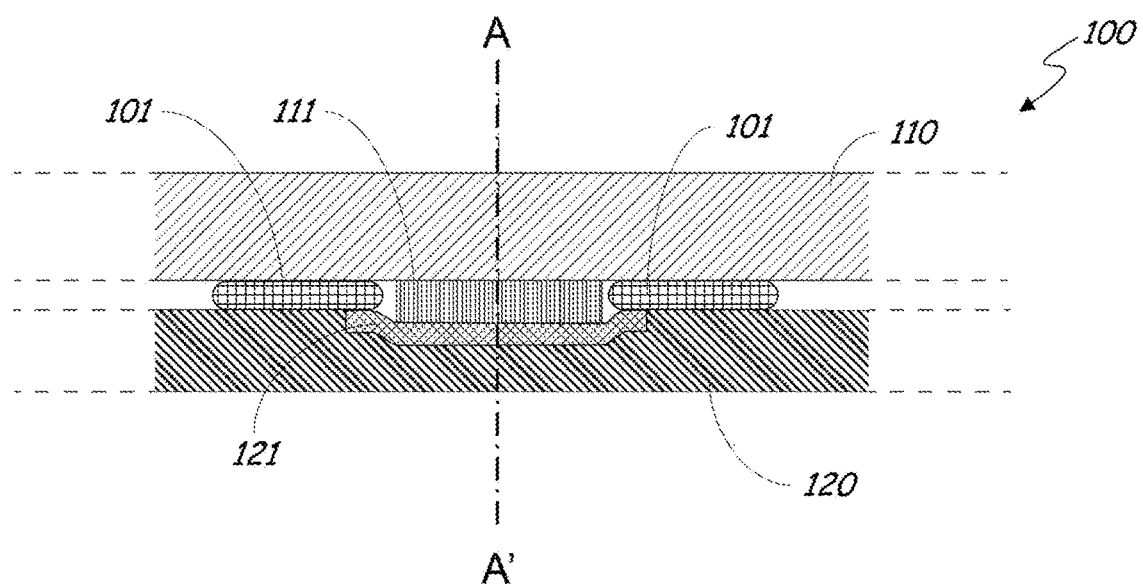

Features and advantages of the invention will be described in detail, with reference to the figures, in the following description. In the figures, the various parts are not in scale and the widths of some areas, and especially the thickness of some layers, may be greatly increased for clarity of representation; in addition, in all figures, to like reference numerals correspond like elements.

The interconnection system of the invention allows obtaining a stable electrical connection between an elastic and extensible substrate on which there is at least one extensible conductive structure and at least one external conductor; the adhesive and electrically insulating material interposed between the interconnection board and the elastic and extensible substrate is in turn preferably elastic, although this is not a necessary condition for the implementation of the invention. The elastic and extensible substrate and the interconnection board generally have conductive structures on one face only; the faces of said board and said substrate on which are present the conductive structures are defined "functionalized faces" in the present description and in the claims.

Figure 1B:
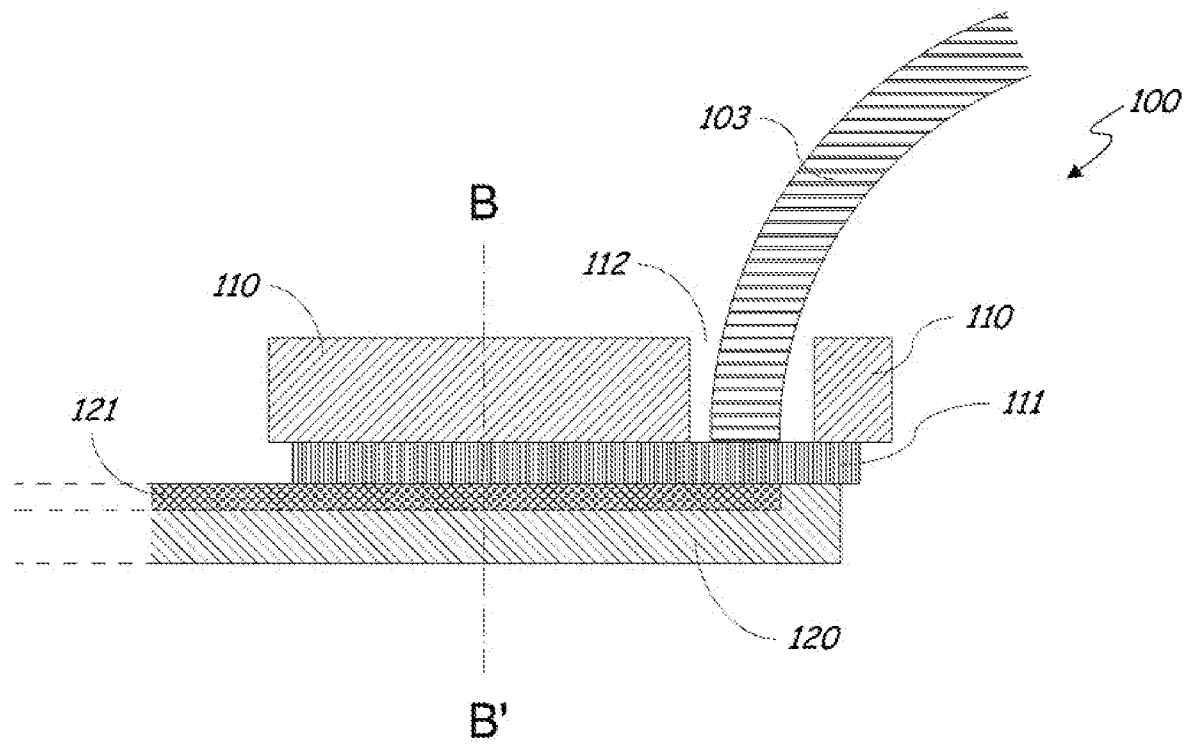

A first embodiment of the interconnection system of the invention is shown in FIGS. 1A and 1B. These Figures show views of the system in two mutually orthogonal sections: in particular, the view in FIG. 1A is a section along the dotted line B-B' in FIG. 1B, and the view in FIG. 1B is a section along the dotted line A-A' in FIG. 1A. FIG. 1A shows, for simplicity, the connection between a single conductive track on the interconnection board and a single extensible conductive structure on the elastic and extensible substrate but, as described hereinafter, the interconnection systems of the invention typically connect multiple conductors external to the system (hereinafter simply "external conductors") to multiple extensible conductive structures; the most common case is that external conductors and extensible conductive structures are in equal number and connected in a "one to one" mode, but systems in multiplexing mode may also be implemented, in which multiple extensible conductive structures are contacted with a single external conductor.

System 100 in FIGS. 1A and 1B consists of a planar and non-extensible board 110 with a conductive track 111 on a functionalized face thereof; an elastic and extensible substrate 120, on a functionalized face of which is present the extensible conductive structure 121 exposed on the surface of the substrate; and at least one deposit 101 of an electrically insulating, preferably elastic adhesive material interposed between said board 110 and substrate 120. Board 110 and substrate 120 have the respective functionalized faces facing each other and deposit 101 adheres to these functionalized faces. In practice, when board 110 and substrate 120 are put in contact with each other, the presence of the protruding track 111 causes the formation of an empty space between the functionalized faces of board and substrate, which is then filled with the material of deposit 101. The coupling between board 110 and substrate 120 through the material of deposit 101 is accomplished by applying a force (shown by arrows 500) that holds track 111 pressed against the extensible conductive structure 121, thus elastically deforming it along with substrate 120; this condition is shown in FIG. 1A, which shows how substrate 120 and structure 121 are deformed by compression in the area in contact with track 111. In this way, the material of deposit 101 ensures the adhesion between substrate and board, maintaining a residual pressure between track 111 and structure 121 even after removal of the force applied during assembly, as shown in FIG. 1A'. In the preferred case in which deposit 101 is elastic, it also ensures that said track and said extensible conductive structure remain in contact also in case of their relative motions in the directions of the plane parallel to the functionalized faces; these movements may be along a direction parallel to the axis of track 111 and structure 121, along a direction orthogonal to this axis, so that track 111 and structure 121 move sideways relative to each other, or along directions which are combinations of these two main directions. The area covered by deposits 101 is wide enough to absorb the stress generated during deformation of the contact, without causing breakage thereof when the elastic and extensible substrate 120 is deformed to the normal elongation degrees to which it may be subjected by the movements of the human body following the implantation into the same.

At one end of board 110 (see FIG. 1B) an external conductor 103 is present for the electrical connection of the system with external devices, for example an electrical signal recording system or electrical stimulation system for neurophysiology, in case of use of the extensible conductive structures as electrodes for neuromodulation; this conductor may be of any type, for example rigid, elastic but not extensible or in turn extensible; typically, the external conductor 103 is an electric wire, for example made of copper. Conductor 103 is in electrical contact with track 111 through an opening 112 in board 110. The specific methods for establishing a connection between conductor 103 and track 111 through opening 112 are illustrated below.

Figure 2:
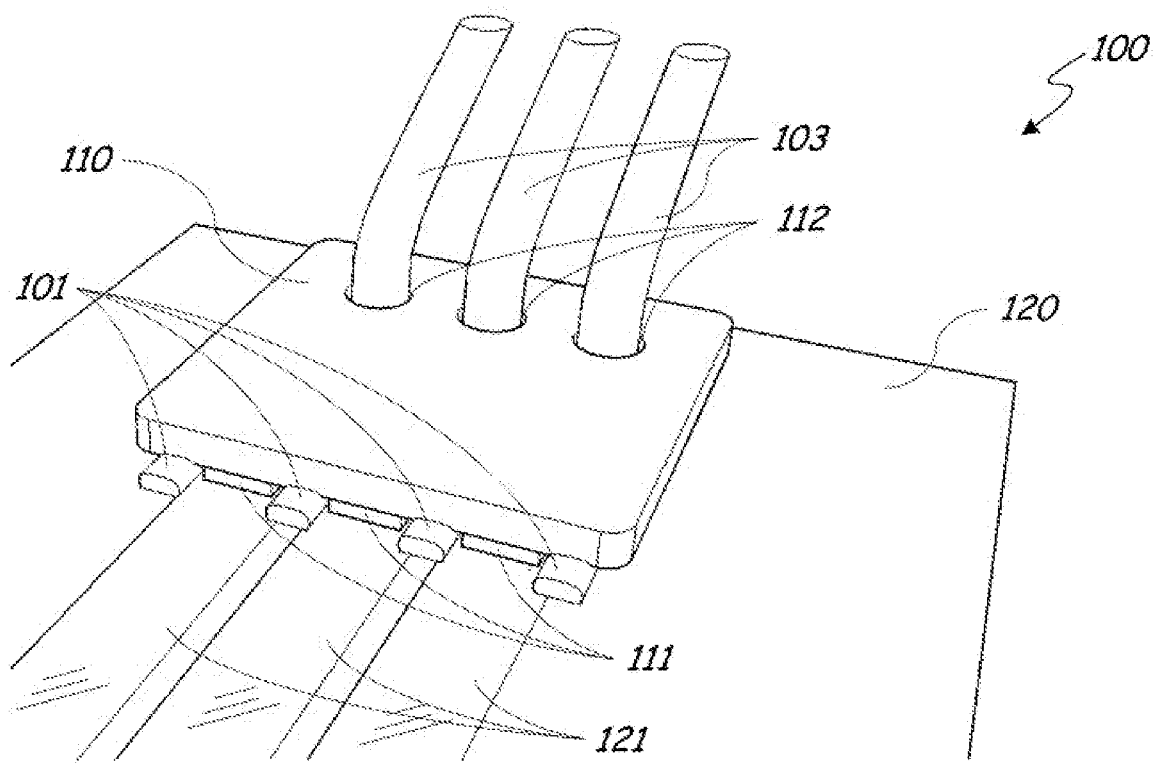
FIG. 2 shows a perspective view of a system of FIGS. 1A, 1A' and 1B.

As mentioned above, FIGS. 1A, 1A' and 1B show a system in which a single interconnection is established between a track 111 and a conductive structure 121, but the system of the invention is particularly useful to implement multiple interconnections between multiple external conductors and multiple extensible conductive structures, which may be in number equal to or different than the external conductors. FIG. 2 shows a perspective view of an interconnection system 100; in this figure, for simplicity, the mild depression of structures 121 at tracks 111 is not shown. There are three tracks 111 on board 110, in contact with as many extensible conductive structures 121 present on the elastic and extensible substrate 120; the three tracks are then connected to three external conductors 103, via through holes 112 in board 110; the figure also shows the placement, in this embodiment of the interconnection system of the invention, of deposits 101.

For the production of the components of the system of the invention, all the materials that have suitable physical and chemical properties may be used. As examples, we may mention:

- for the construction of board 110, an electrically insulating material may be used, usually made of a polymeric material; the board may be rigid or preferably flexible, but non-extensible; typically, this board is of the same type as those used for the production of printed circuit boards (PCBs);
- tracks 111 are made of metal, for example copper, silver, gold, platinum or cobalt-nickel based alloys, and may be deposited with any known technique, such as the technique of coating the whole face of the board with metal, masking with inks of the parts corresponding to the tracks to be produced, and selective removal of non-masked metal parts with chemical etchings (typically acid baths); or, alternately, with selective deposition techniques through masking (e.g. sputtering);
- for the elastic and extensible substrate 120, any elastomeric polymer material may be used; examples of such materials are polyurethane elastomers, elastomeric fluoropolymers, polyolefin-based elastomers, polybutadiene (BR), styrene-butadiene rubbers (SBR), ethylene-propylene rubbers (EPR), ethylene-propylene-diene rubbers (EPDM), nitrile rubbers (NBR), acrylic rubbers (ACM), the rubbers based on isobutylene and isoprene (IIR), and preferably silicones (polysiloxanes);
- the extensible conductive structures 121 on the substrate are made by implanting particles of conductive materials, typically metals (such as gold) in the surface of the substrate; the preferred technique to achieve implantation is "Supersonic Cluster Beam Implantation" or SCBI, described in patent application WO 2011/121017 A1 assigned to the present Applicant;
- the adhesive material for making deposits 101 may be non-elastic, such as an epoxy resin or another polymer; preferably, though, said material is elastic and is typically a silicone;
- finally, the external conductors 103 may be of any known type, for example a cable or a braid of metal covered with insulating material.

Figure 3A:
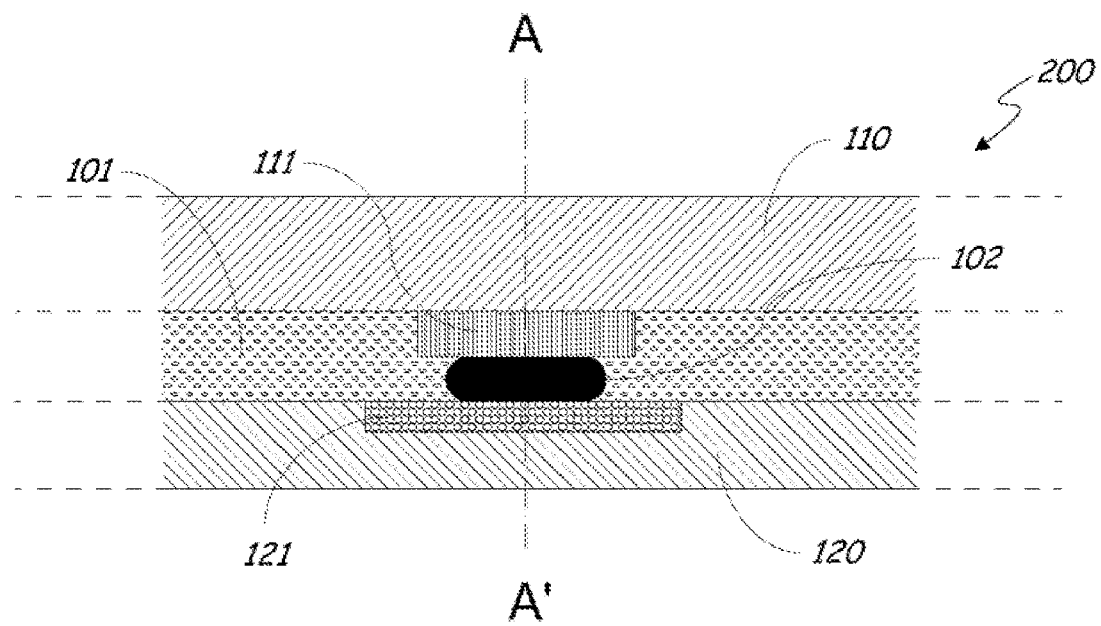
FIGS. 3A and 3B show two sectional views of a system according to a second embodiment of the invention.
Figure 3B:
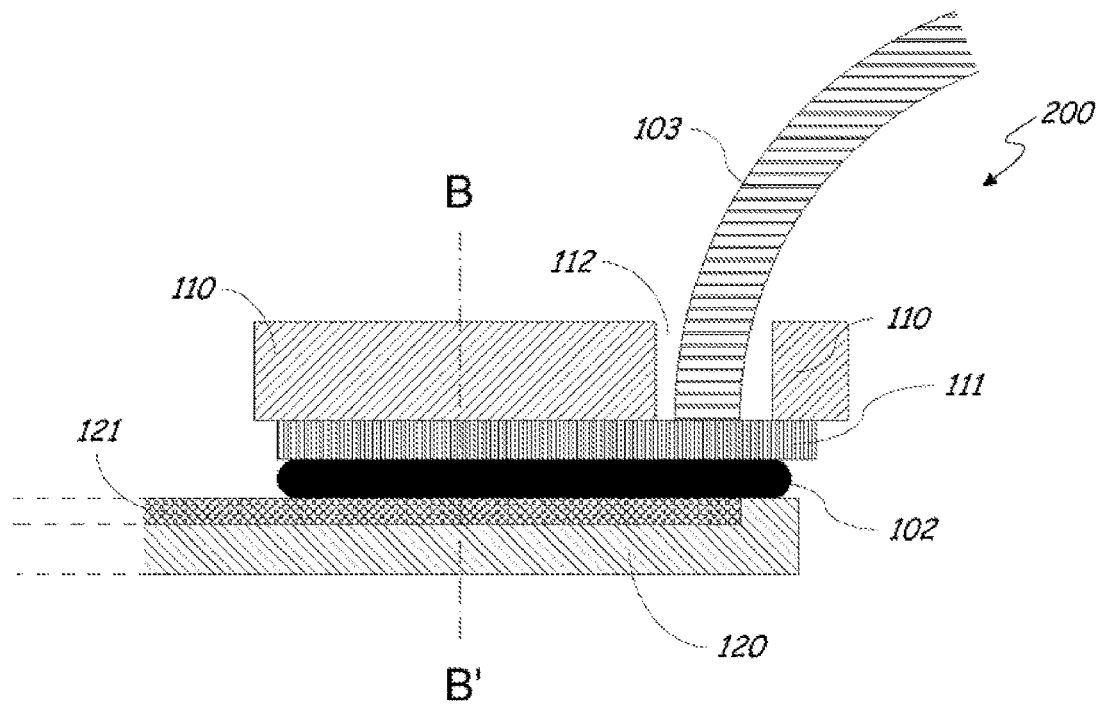

In a second embodiment, the system of the invention (200) further comprises an additional deposit of an elastic, adhesive and electrically conductive material, interposed between the track on the board and the conductive structure on the elastic and extensible substrate. This embodiment is shown in FIGS. 3A and 3B, representing views in two mutually orthogonal sections similar to those in FIGS. 1A and 1B (the view in FIG. 3A is a section along the dotted line B-B' in FIG. 3B and the view in FIG. 3B is a section along the dotted line A-A' in FIG. 3A); also FIGS. 3A and 3B show, for convenience, only one interconnection between a track and an extensible conductive structure.

System 200 consists of a planar and non-extensible board 110 with a conductive track 111 on a face thereof; an elastic and extensible substrate 120, on a face of which is present the extensible conductive structure 121; and at least one deposit 101 of an electrically insulating, preferably elastic adhesive material interposed between the functionalized faces of said board 110 and substrate 120. In this case, however, track 111 and the extensible conductive structure 121 are not in direct contact with each other, but through a deposit 102 of an elastic, adhesive and electrically conductive material, that adheres to both cited elements and ensures electrical continuity between them. With this configuration, the electrical contact between track 111 and conductive structure 121 is guaranteed, in addition to relative movements in the plane, also for small movements perpendicular to the plane of the functionalized faces, i.e. movements that move track 111 away from structure 121; moreover, this configuration increases the adhesion surface (and thus the adhesion strength) between board 110 and substrate 120.

The materials for producing a system of type 200 are the same as mentioned for the first embodiment; the same material used for deposits 101 is used for the production of deposits 102, but charged with conductive particles, typically metallic and preferably silver powder, to make the deposit electrically conductive. Materials useful for this purpose are described in U.S. Pat. No. 7,537,712 B2, entitled "Electrically conductive silicone rubber composition".

Figure 4:
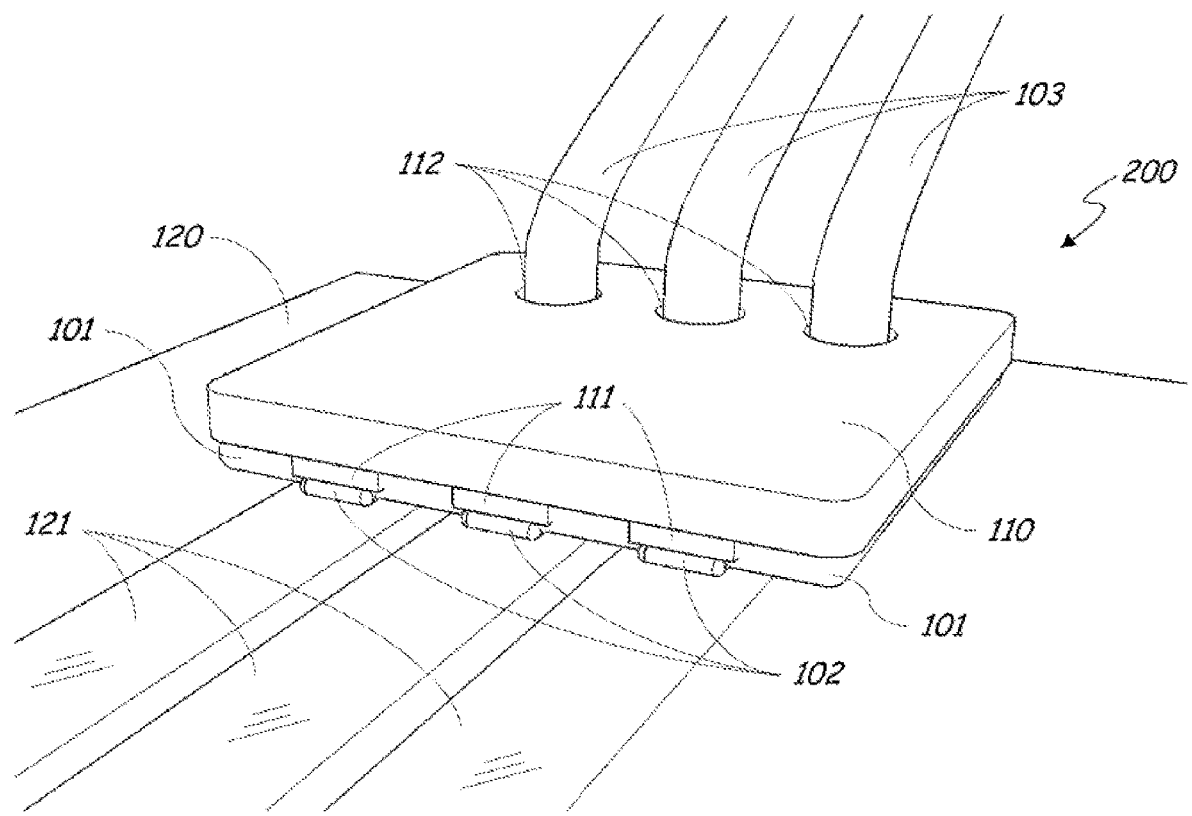
FIG. 4 shows a perspective view of a system of FIGS. 3A and 3B.

FIG. 4 shows a perspective view of a system 200, according to this second embodiment; in this case too, three conductive paths are shown, each consisting of an external conductor 103, a track 111, a deposit 102 of elastic electricity conductive material, and an extensible conductive structure 121.

Figure 5:
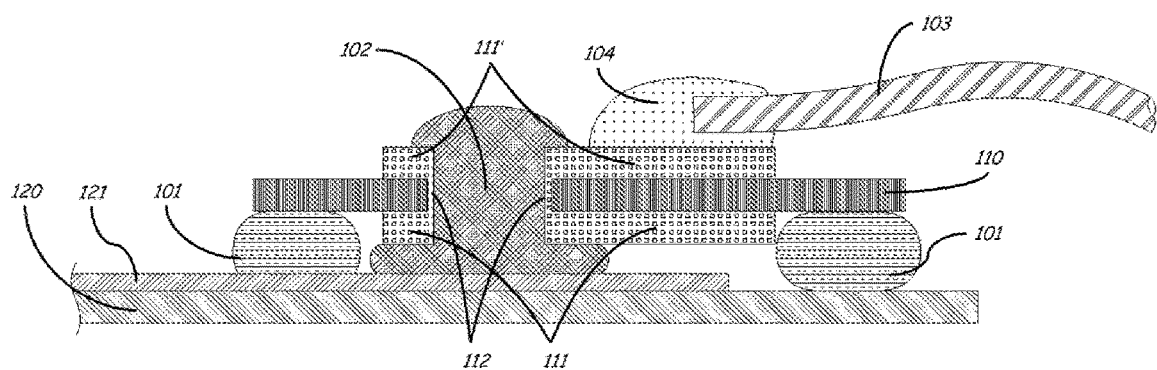
FIG. 5 shows a sectional view of a particular embodiment of the electrical connection between the external conductor and the extensible conductive structure.

The connection between the external conductors 103 and tracks 111 can be implemented by any means and technique known to the man skilled in the art, such as welding (thermal welding, laser welding, ultrasonic welding), soldering, mechanical fastening or gluing with conductive glues of any kind. In a typical embodiment, the connection is made by means of through holes ("via holes") 112 made on board 110, filled with a conductive material (e.g. tin) in which one end of conductor 103 is embedded. Alternatively, the method outlined in FIG. 5 may be used. In this method, the interconnection between the extensible device and conductor 103 is achieved with a double-face interconnection board, consisting of a planar non-extensible board 110 having conductive tracks made of Cu plated with Au on both its faces. On the lower face of board 110 (the one facing the extensible conductive structure 121) there are one or more first tracks 111; on the upper face of board 110 there are one or more second tracks 111'. Each second track 111' is connected to a first track 111 through a through hole 112 which is also coated with a metal (typically Au) inside, as shown in section in FIG. 5. The external conductor 103 is connected to the upper conductive track 111' through a deposit of conductive material 104 (such as tin). The extensible conductive structure 121 is connected to track 111 through a deposit 102 of elastic, adhesive and electrically conducting material which in this alternative embodiment is dispensed through the through hole. This ensures the electrical connection between structure 121 and the external conductor 103, through the through holes 112, the upper tracks 111' and the conductive material 104. A deposit 101 of an electrically insulating and preferably elastic adhesive material, interposed between board 110 and substrate 120 (and/or between board 110 and structure 121) ensures an additional mechanical coupling between the connection board and the intrinsically extensible device.

In all cases, the external conductor can be welded to track 111 (or to track 111') or glued with a conductive paste or glue.

The system of the invention allows overcoming various problems in the electrical connection between extensible and non-extensible parts. A solution using simply a conductive glue to put a non-extensible wire in electrical contact with an extensible conductive structure, that is, without using the interconnection board of the present invention, would not produce the same results. In fact, even if a contact manufactured in this way would be able to ensure an electrical contact in the absence of mechanical stress, due to low contact surface available on the wire and the large discrepancy between the mechanical properties of the two glued parts, in the presence of said stress the system could easily break, because stress builds up at the interface with the contact wire. Moreover, this solution would be even more unstable towards twisting strains. Finally, if multiple contacts on the same device are to be implemented, a direct contact system, through the silicone glue alone, would become cumbersome and difficult to implement.

The inventors have instead surprisingly observed that these problems do not occur with the system of the present invention, as this allows obtaining a large contact surface between the rigid (or non-extensible) conductor and the extensible one, so that the mechanical forces due to the relative motions of the two parts are distributed over a larger area, thereby preventing the localization of stress on the electrical contact and allowing the interconnection of many contacts to be obtained in an efficient manner.

In particular, it was observed that through the present invention, the system remains under conditions of electrical conduction when the shear stress is such as to cause an elongation of at least 5% of the extensible part and stress builds up between the rigid wire and the elastic and extensible substrate.

Summing up, the following advantages and features are obtained with the system of the invention:

1: an electrical contact can be obtained between at least one intrinsically extensive conductive structure and a non-extensible conductive part, such as a wire;

2: a stable electrical contact can be maintained even when a shear stress is applied to the system consisting of an extensible structure and a non-extensible part;

3: a stable electrical contact can be maintained even when a torque stress is applied to the non-extensible part with respect to the extensible structure;

4: the interconnection system allows establishing electrical contacts in parallel between different intrinsically extensible conductive structures and the respective non-extensible parts (such as for example a multiplicity of wires);

5: the footprint of the entire interconnection is thin enough to make possible the implementation of devices like neuromodulation electrodes, which must generally be used in small areas of the human body.

The invention will be further described by the following examples.

Example 1

Figure 6:
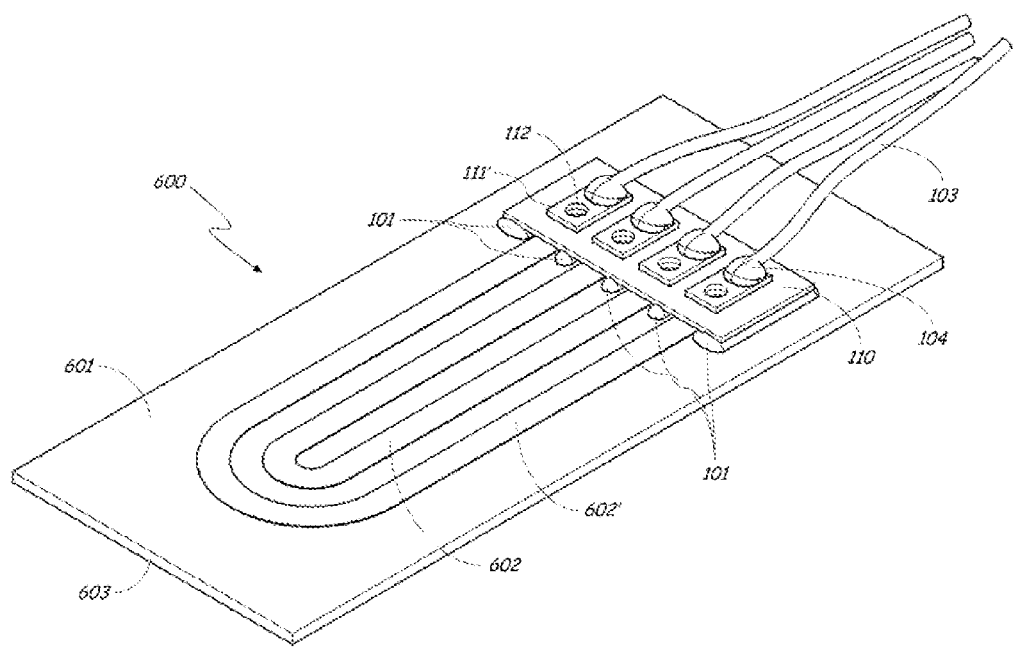
FIGS. 6 and 7 show two possible geometries of systems formed by extensible substrates on which are present extensible conductive structures connected to external conductors according to the invention.

This example refers to the production of a system of the invention consisting of the union of an extensible conductive structure with copper conductive wires; the system, 600, is shown in FIG. 6.

The elastic and extensible substrate 601 is 200 μm thick and is made of two-component silicone rubber; it is obtained by dispersing on a glass support 1 gram of liquid silicone (MED-6033 of the company NuSil Technology LLC, Carpinteria, Calif., USA), spread by the spin coating technique and polymerized for 30 minutes at 150° C. according to the manufacturer's instructions.

Two extensible U-shaped metal tracks, 602 and 602', are obtained in the substrate thus produced, placed the first one into the second one as shown in the figure. These tracks consist of 20 nm thick platinum deposits obtained through SCBI, as described in patent application WO 2011/121017 A1, protecting the substrate using a metal mask (stencil mask) of the desired shape. Thereafter, a 150 nm layer of gold exactly overlapping that of platinum is implanted through SCBI using the same setup described above. The tracks are 0.7 mm wide and are mutually spaced by 0.3 mm. The length of the outer U track is 21 mm, while the inner one is 18 mm. The metal tracks thus obtained constitute the extensible conductive structures of the invention. The interconnection between the extensible metal tracks and the conductive copper wires 103 is obtained with an interconnection board 110, where the connection mode is the one described above with reference to FIG. 5, and consisting of a double-sided printed circuit board. Board 100 consists of a polymeric support made of FR4 (an epoxy resin reinforced with glass fibres, standard in the field) having a length of 2 mm, width of 4.5 mm and thickness of 0.1 mm, on which are arranged four conductive tracks (111, not shown in the figure) made of Cu plated with Au (size: 1.2 mm×0.7 mm×50 μm). The Cu/Au conductive tracks are present on both faces of the board. Each track is connected with the underlying one through a through hole 112, whose inner walls are in turn coated with Au. A silicon glue (101) consisting of two-component liquid silicone Nusil MED 6033 is distributed on the silicone rubber, interposed between one conductive track and the other. The interconnection board is placed on the silicone substrate, so as to match the four lower tracks with the four end parts of the extensible conductive structures 602 and 602'. A force is applied to the interconnection board equal to 1 N, evenly distributed on the board surface and perpendicular to the surface itself, so as to press it on the silicone substrate.

This ensures both the electrical contact between the extensible tracks and the Cu/Au conductive tracks of board 110, and the mechanical coupling between board and elastic and extensible silicone substrate by the adhesive material 101. The force that presses the interconnection board on the silicone substrate is maintained as long as necessary for the hardening of material 101, which is obtained by baking in a furnace at 70° C. for 60 minutes.

Once material 101 has hardened, four copper wires (103) of 0.1 mm diameter are connected by tin soldering to the four parts 111' of Cu/Al present on the upper surface of board 110, and in contact with tracks 111 through the gold present in the through holes 112; each of the four copper wires is electrically insulated with a polymer coating.

In this way, the interconnection between a non-extensible electrical conductor (copper wire) and an intrinsically extensible electrical conductor (Pt/Au tracks deposited on silicone rubber), through an interconnection board is completed. The upper face of board 110 is coated with an epoxy resin (not shown in figure) in order to electrically insulate and mechanically reinforce the tin soldered area.

Each end of tracks 602 and 602' is connected to a copper wire. In order to check the hold of the electrical interconnection under mechanical stress, the following is carried out: a potential difference of 1 V is applied between two copper wires interconnected to the two ends of the same extensible track and the electrical resistance of the system is measured. The device is subjected to tensile stress, holding it by the copper wires on the one end, and by end 603 of the silicone substrate on the other. A resistance of about 200Ω is measured at rest. Under tensile stress, resistance values of about 270Ω, 390Ω and 880Ω are observed, for silicone substrate extensions equal to 5%, 10%, 20%, respectively. Returning the device to rest position, the resistance returns to a value of 200Ω.

Example 2

Figure 7:
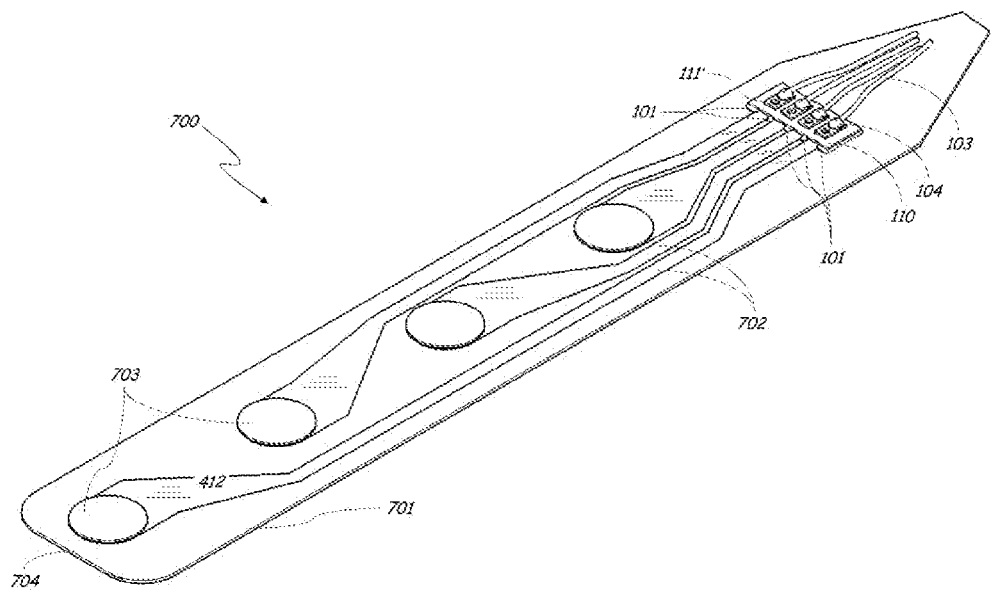

This example refers to the production of another system of the invention consisting of the union of an extensible conductive structure with copper conductive wires; the system, 700, is shown in FIG. 7.

The procedure outlined in Example 1 for the coupling between an elastic and extensible substrate and an interconnection board 110 to which four copper wires 103 are connected is repeated, with the only difference of the different structure of the extensible conductive structure.

The extensible part of the system consists of an elastic and extensible substrate 701 on which four extensible metal tracks 702 of Au/Pt are present, terminated by an electrode of Pt, 703, also extensible. In their narrowest part (the one closest to the interconnect board), the tracks are 0.7 mm wide and mutually spaced by 0.3 mm; the four tracks are 12, 22, 32 and 44 mm long, respectively. The Pt electrodes (703) are circular, with a diameter of 3.5 mm. The tracks are made through deposition of Pt and Au nanoparticles on a silicone rubber substrate about 200 μm thick; substrate and tracks are produced as described in example 1. In detail, the tracks are obtained by depositing a 20 nm Pt layer and then a 75 nm thick Au layer; electrodes 703 are obtained by depositing 150 nm Pt and partially overlaying the Pt/Au tracks on the Pt electrode to ensure electrical continuity between the two elements. The tracks and electrodes thus obtained constitute, together with the silicone substrate, an intrinsically extensible conductive composite material.

After the coupling between board and extensible conductive structure, the entire system (except for the copper wires 103) is coated with a 200 μm thick layer of silicone rubber, leaving only the Pt electrodes exposed.

The device is immersed in a saline solution, keeping the free end of the copper wires outside the solution. A counter electrode is also added to the solution consisting of a Pt rod and between the counter electrode and each of the four extensible electrodes, one at a time, an electric current is flown by applying a potential difference of 1 V. The circuit impedance is measured and recorded for each of the four tracks 702; the measured values are 170, 175, 179 and 183Ω, respectively. In order to check the hold of the electrical interconnection to mechanical fatigue, the device is then subjected to 1000 elongation cycles, keeping it on one end by the copper wires, and on the other end by the end (704) of the extensible structure that is furthest from the interconnection board. In each cycle, the extensible structure is stretched by 10% of its length at rest, and then brought back to the original length, at a rate of 1 mm/s. At the end of 1000 cycles, the system is again immersed into the saline solution, and the measurement of the four impedance values is repeated, obtaining values of 175, 180, 182 and 191Ω, respectively, slightly higher than those recorded on the system immediately after its production; this demonstrates the mechanical fatigue strength of the interconnection between copper wires and extensible structure.

Example 3

The procedure of Example 2 is repeated.

In this case, the four through holes 112 on board 110 are filled with conductive silicone CV 2644 (NuSil), prepared according to the manufacturer's instructions; the conductivity of conductive silicone is due to the presence of Ag particles therein. The conductive silicone is loaded into a syringe and dispensed within each via through a needle. The conductive silicone fills hole 112, thus creating the electrical contact between the underlying extensible conductive track and the Cu/Au metal conductive tracks of the interconnection board. The device is baked at 70° C. for one hour, so as to cure the conductive silicone. On the resulting system, following the method of Example 2, impedance is measured for each of the four tracks and four electrical contacts 703, obtaining values of 173, 177, 182 and 185Ω.

The system is then subjected to the same fatigue program of Example 2 (1000 cycles of elongation by 10% of the length of the system at rest, and back to the original length, at a rate of 1 mm/s).

At the end of the fatigue program, the impedance is again measured for each of the four tracks and four electrical contacts 703, obtaining values of 177, 180, 187 and 191 Ω respectively, slightly higher than those registered on the system just produced, demonstrating the mechanical fatigue strength of the interconnection between copper wires and extensible structure.

The invention claimed is:

1. An implantable system of electrical interconnection between an intrinsically extensible conductor and a not intrinsically extensible one, or between two extensible conductors, comprising:
    an interconnection board comprising a rigid or flexible non-extensible planar substrate, on a first functionalized face of which is present at least one conductive track, each in electrical contact, at one end thereof, with at least one conductor external to the system, which may be rigid, elastic, or in its turn extensible;
    an elastic and extensible substrate on a second functionalized face of which is present at least one extensible conductive structure, wherein the elastic and extensible substrate and the at least one extensible conductive structure are extensible in a plane parallel to the first and second functionalized faces; and
    at least one deposit of an adhesive, elastic, and electrically insulating material, interposed between said interconnection board and said elastic and extensible substrate, which adheres to said first and second functionalized faces at least in part of their zones free from said at least one conductive track and said at least one extensible conductive structure, establishing adhesion between said interconnection board and said elastic and extensible substrate while allowing relative motion thereof and ensuring electrical contact between said at least one conductive track and said at least one extensible conductive structure upon the relative motion.

2. The implantable system according to claim 1, wherein said at least one conductive track is protruding with respect to the surface of the interconnection board and causes the presence of a space between the first and second functionalized faces, said space being filled with the deposit of the adhesive, elastic, and electrically insulating material.

3. The implantable system according to claim 1, wherein said at least one conductive track is in electrical contact with said at least one extensible conductive structure through the deposit of the elastic, adhesive, and electrically conductive material, which adheres to said at least one conductive track and said at least one extensible conductive structure.

4. The implantable system according to claim 1, wherein the electrical connection between the at least one external conductor and the at least one conductive track is realized by thermal welding, laser welding, ultrasonic welding, brazing, mechanical fastening, or bonding with conductive glues.

5. The implantable system according to claim 1, wherein the electrical connection between the at least one external conductor and the at least one conductive track is made via a through hole formed in said interconnection board.

6. The implantable system according to claim 5, wherein said through hole is filled with a conductive material in which one end of the at least one external conductor is embedded.

7. The implantable system according to claim 5, wherein:
the interconnection board has, on its face opposite to that facing the at least one extensible conductive structure, at least one second conductive track electrically connected to a first conductive track present on the first functionalized face through a metallization of one or more walls of the through hole;
the at least one external conductor is connected to said at least one second conductive track through a deposit of conductive material; and
the at least one extensible conductive structure is connected to the first conductive track-through the deposit of the elastic, adhesive, and electrically conducting material inserted in the through hole.

8. The implantable system according to claim 7, wherein:
the interconnection board is made of an electrically insulating, rigid, or flexible but non-extensible material;
the first conductive track and the at least one second conductive track are made of metal;
the at least one extensible substrate is made of a material selected from polyurethane elastomers, elastomeric fluoropolymers, polyolefin-based elastomers, polybutadiene (BR), styrene-butadiene rubbers (SBR), ethylene-propylene rubbers (EPR), ethylene-propylene-diene rubbers (EPDM), nitrile rubbers (NBR), acrylic rubbers (ACM), rubbers based on isobutylene and isoprene (IIR), or silicones (polysiloxanes);
the at least one extensible conductive structure is formed by particles of conductive materials; and
the deposit of the adhesive, elastic, and electrically insulating material, are made of silicone.

9. The implantable system according to claim 8, wherein the interconnection board is made of a polymeric material.

10. The implantable system according to claim 8, wherein the first conductive track and the at least one second conductive track are made of a material selected from copper, silver, gold, platinum, or one or more alloys based on nickel-cobalt.

11. The implantable system according to claim 8, wherein the at least one extensible conductive structure is formed by particles of a material selected from silver, gold, or platinum.

12. The implantable system according to claim 1, wherein at least a first portion of the at least one extensible conductive structure and at least a second portion of the at least one conductive track are in direct contact.

13. The implantable system according to claim 1, wherein the deposit of the adhesive, elastic, and electrically insulating material establishes the adhesion while further allowing additional relative motion between said interconnection board and said at least one extensible substrate in a direction parallel to the plane, or parallel or orthogonal to an axis of the at least one conductive track or the at least one extensible conductive structure, and ensuring electrical contact between said at least one conductive track and said at least one extensible conductive structure upon the additional relative motion.

* * * * *